US008461531B2

(12) United States Patent
Tillotson

(10) Patent No.: US 8,461,531 B2
(45) Date of Patent: Jun. 11, 2013

(54) DETECTING VOLCANIC ASH IN JET ENGINE EXHAUST

(75) Inventor: Brian J. Tillotson, Kent, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 13/270,286

(22) Filed: Oct. 11, 2011

(65) Prior Publication Data

US 2013/0087708 A1    Apr. 11, 2013

(51) Int. Cl.
*G01N 21/00* (2006.01)
(52) U.S. Cl.
USPC .............. 250/338.5; 250/338.1; 250/339.13
(58) Field of Classification Search
USPC ...................................................... 250/338.5
See application file for complete search history.

(56) References Cited

U.S. PATENT DOCUMENTS

| | | | |
|---|---|---|---|
| 4,481,417 A * | 11/1984 | Inglee ......................... | 250/338.1 |
| 4,965,573 A * | 10/1990 | Gallagher et al. ............ | 340/968 |
| 5,241,315 A | 8/1993 | Spinhirne | |
| 5,475,223 A * | 12/1995 | Carter, III ................ | 250/339.13 |
| 5,602,543 A | 2/1997 | Prata et al. | |
| 5,612,676 A * | 3/1997 | Plimpton et al. .............. | 340/578 |
| 5,654,700 A | 8/1997 | Prata et al. | |
| 5,767,519 A | 6/1998 | Gelbwachs | |
| 5,797,682 A * | 8/1998 | Kert et al. ..................... | 374/123 |
| 5,999,652 A * | 12/1999 | Bushman ..................... | 382/221 |
| 6,404,494 B1 | 6/2002 | Masonis et al. | |
| 6,490,530 B1 | 12/2002 | Wyatt | |
| 7,034,935 B1 | 4/2006 | Kruzelecky | |
| 7,365,674 B2 | 4/2008 | Tillotson et al. | |
| 7,383,131 B1 | 6/2008 | Wey et al. | |
| 7,557,734 B2 | 7/2009 | Estrada, III et al. | |
| 7,566,881 B2 | 7/2009 | Parvin et al. | |
| 7,592,955 B2 | 9/2009 | Tillotson et al. | |
| 7,598,901 B2 | 10/2009 | Tillotson et al. | |
| 7,609,463 B2 | 10/2009 | Tsao | |
| 7,656,526 B1 | 2/2010 | Spuler et al. | |
| 7,689,328 B2 | 3/2010 | Spinelli | |
| 7,734,411 B2 | 6/2010 | Gremmert | |
| 7,735,352 B2 | 6/2010 | Alm et al. | |
| 7,743,641 B2 | 6/2010 | Bailey et al. | |
| 7,755,515 B2 | 7/2010 | Hagan | |
| 2005/0120707 A1* | 6/2005 | Pizzi ............................... | 60/278 |
| 2008/0099630 A1 | 5/2008 | Parikh et al. | |

(Continued)

FOREIGN PATENT DOCUMENTS

AU    2011100797 A4    8/2011

OTHER PUBLICATIONS

Ao et al., "Lower-Troposphere Refractivity Bias in GPS Occultation Retrievals", J. Geophys. Res., vol. 108, Issue D18 (2003).

(Continued)

*Primary Examiner* — Marcus Taningco
(74) *Attorney, Agent, or Firm* — Ostrager Chong Flaherty & Broitman P.C.

(57) ABSTRACT

Onboard systems and methods for early detection that an aircraft has flown into a volcanic ash plume embedded within a water vapor cloud having a concentration of a volcanic ash which would be dangerous to an aircraft. The detection method generally comprises the steps of measuring the infrared emission characteristics of a jet engine exhaust and generating a detection signal when the intensity of infrared emissions at or near a spectral peak wavelength exceeds a threshold.

22 Claims, 8 Drawing Sheets

U.S. PATENT DOCUMENTS

| | | | |
|---|---|---|---|
| 2009/0189802 | A1 | 7/2009 | Tillotson et al. |
| 2009/0229250 | A1* | 9/2009 | Yamakage et al. ............. 60/276 |
| 2009/0272270 | A1 | 11/2009 | McGill et al. |
| 2012/0191350 | A1* | 7/2012 | Prata et al. ........................ 702/3 |

OTHER PUBLICATIONS

Bouttier et al., Data Assimilation Concepts and Methods, Mar. 1999, Chapter 10, "Four-Dimensional Variational Assimilation (4D-Var)".

http://volcanoes.usgs.gov/hazards/gas/index.php.

http://volcano.oregonstate.edu/education/gases/comp.html.

Spinetti et al. "Mt. Etna Volcanic Aerosol and Ash Retrievals Using MERIS and AATSR Data", Proc. 2nd MERIS/(A)ASTR User Workshop, Frascati, Italy, Sep. 22-26, 2008 (ESA SP-666, Nov. 2008).

Schumann et al., "Report of Falcon Flight 19DLR;s Research Aircraft 'Falcon 20E' Completes Apr. 2010", Deutsches Zentrum fur Luft-und Raumfahrt.

DLR's Research Aircraft "Falcon 20E" Completes Measurement Flight Successfully, Apr. 19, 2010, Deutsches Zentrum fur Luft-und Raumfahrt.

Chazette, "Sensing and Monitoring Volcanic Ash for Air Travel Safety Using LabVIEW and PXI", Product Design & Development, Jul. 20, 2010.

Carr, The Aerosol Models in MODTRAN: Incorporating Selected Measurements from Northern Australia, DSTO Defence Science and Technology Organisation, Edinburgh, South Australia, Dec. 2005.

Kneizys et al., The MODTRAN 2/3 Report and LOWTRAN 7 Model, Philips Laboratory, Geophysics Directorate, Hanscom AFB, Massachusetts, Jan. 11, 1996.

Extended European Search Report dated Jan. 22, 2013 in corresponding European Patent Application No. 12187364.0.

Clarisse, L. et al., "A Correlation Method for Volcanic Ash Detection Using Hyperspectral Infrared Measurements," Geophysical Research Letters, vol. 37, L19806, Oct. 12, 2010, American Geophysical Union, Washington D.C.

Guffanti, M. et al., "Reducing the Threat to Aviation From Airborne Volcanic Ash," Presented at 55th Annual International Air Safety Seminar, Nov. 4-7, 2002, Dublin, retrieved from the Internet: URL:http://volcanoes.usgs.gov/ash/trans/aviation_threat.html, Jan. 10, 2013, U.S. Geological Survey, Reston, Virginia.

Haschberger, P., "Spectrometric Inflight Measurement of Aircraft Exhaust Emissions: First Results of the Jun. 1995 Campaign," Journal of Geophysical Research, vol. 101, No. D20, pp. 25,995-26,006, Nov. 20, 1996, American Geophysical Union, Washington D.C.

Hilton, M. et al., "Detection of Soot Particles in Gas Turbine Engine Combustion Gases Using Non-Intrusive FTIR Spectroscopy," Part of the EUROPTO Conference on Spectroscopic Atmospheric Environmental Monitoring Techniques, Barcelona, Spain, SPIE vol. 3493, Oct. 9, 1998, pp. 20-31, XP055049179, retrieved from the Internet: URL:http://proceedings.spiedigitallibrary.org/ on Jan. 10, 2013.

* cited by examiner

DETECTING VOLCANIC ASH IN JET ENGINE EXHAUST

TECHNICAL FIELD

This disclosure generally relates to systems and methods for sensing when an aircraft is encountering a volcanic ash plume and, more particularly, to systems and methods for onboard detection of volcanic ash plumes embedded in water vapor clouds.

BACKGROUND

As used herein, the term "volcanic plume" or "volcanic ash plume" means a cloud of volcanic ash, the term "volcanic gases" means gases given off by active volcanoes, and the term "gas plume" means a plume of a volcanic gas. Dispersed volcanic gases disposed outside the volume occupied by a volcanic ash plume are not included as part of the "volcanic ash plume" as the latter term is used herein.

Volcanic ash can pose a hazard to flying jet aircraft, threaten the health of people and livestock, damage electronics and machinery, and interrupt power generation and telecommunications. Volcanic ash comprises tiny jagged particles of rock and natural glass blasted into the air by a volcano. Wind can carry ash thousands of miles, affecting far greater areas than other volcano hazards.

Volcanic plumes present two problems for aircraft: (a) engine malfunction due to ash; and (b) aircraft damage and/or crew and passenger injury due to ash and corrosive gases. Volcanic ash particles are extremely abrasive. They are jagged particles of rock and glass that can cause rapid wear to the internal workings of jet engines. More important, high temperatures in some parts of jet engines can melt ash that is passed through an engine. The ash then re-solidifies on cooler parts of the engine, forming a layer that blocks airflow, interferes with moving parts, and eventually causes malfunction of the engine. It is therefore desirable for aircraft to be capable of detecting volcanic ash prior to encountering the ash or as quickly as possible thereafter to avoid prolonged exposure to the ash.

Various known solutions for detecting and avoiding a volcanic plume during flight of an aircraft have certain disadvantages. First, for volcanoes that are well monitored, sensors or people on the ground can quickly observe an eruption and report it to flight safety authorities such as the FAA. In these cases, a notice to airmen is issued. However, many remote volcanoes around the world are still not well instrumented and can erupt without immediate detection. Even after detection, the mechanism to issue a notice to airmen imposes a delay for processing and distribution, during which an unwarned aircraft may encounter the plume.

Second, a few satellites are capable of detecting volcanic plumes from orbit, based on the sulfur dioxide spectra, the thermal infrared emission, visible ash clouds, or a combination of these. When a satellite detects a volcanic plume, a notice to airmen is issued. However, satellite observations are not continuous. An eruption that occurs between satellite passes may go undetected for 6 to 12 hours, which is more than enough time for aircraft to encounter the plume. The period of non-detection may go on longer for small eruptions or during overcast conditions. Even after detection, the mechanism to issue a notice to airmen imposes a delay for processing and distribution, during which an unwarned aircraft may encounter the plume.

Third, in daytime clear weather, pilots can visually observe a distinctive volcanic plume and avoid it. Visual observation may be done with the naked eye or with cameras using natural light, infrared emission, optical backscatter measured via lidar or optical backscatter using standard aircraft light sources. Airborne ash particles are exposed and able to reflect light or emit infrared radiation. However, volcanic plumes are often encountered during nighttime and/or embedded within other clouds, such as meteorological clouds containing water droplets or ice crystals, rendering visual detection methods ineffective. In this description, water droplets and ice crystals will be referred to collectively herein as "water precipitate" or "precipitate" for conciseness, and the term "precipitate particles" will refer to droplets of water or crystals of ice embedding ash particles. Meteorological clouds not only surround a volcanic plume, but, because the individual ash particles serve as nucleation sites for precipitate particles, the individual ash particles become embedded in precipitate particles. Therefore, the ash particles are not visible and contribute almost nothing to the electromagnetic signature of the cloud.

Typical uses of infrared emission to detect volcanic plumes use sensors directed toward the natural atmosphere. For example, U.S. Pat. No. 5,654,700, entitled "Detection System for Use in an Aircraft," proposes a system that would detect a volcanic ash cloud ahead of an aircraft by monitoring infrared radiation that traverses the ash cloud. However, the optical and infrared signatures of ash particles that are embedded in precipitate particles are camouflaged and remain hidden from such infrared sensors.

If volcanic ash is not detected, the first sign to an aircraft crew that the aircraft has flown through a water vapor cloud containing volcanic ash is engine failure. A typical pilot response when an engine begins to fail is to increase power. However, when volcanic ash is present, this could make the situation worse. If ash is suspected as the cause of an engine failure, then a pilot may throttle back engines, turn on engine and wing anti-ice devices and lose height to drop below the ash cloud as soon as possible. This action typically helps to restore engine functionality. However, because the aircraft may have already flown through a substantial amount of ash, aircraft parts may have already suffered costly damage which may require maintenance, repair or replacement of engine parts. Therefore, avoiding any amount of flight time through ash helps to reduce any potentially damaging effects of the ash, and therefore helps to save maintenance time and money.

There exists a need for a system that will detect volcanic plumes embedded in clouds and ash particles embedded in precipitate particles, and alert an aircraft to avoid such volcanic plumes, or to rapidly change course to escape such volcanic plumes.

BRIEF SUMMARY

The foregoing purposes, as well as others that will be apparent, are achieved generally by providing a detection system installed onboard an aircraft for detecting volcanic ash in jet engine exhaust and alerting the pilot upon detection of volcanic ash emitted from the jet engine. Such a system provides for reliable detection of volcanic ash particles even when they are embedded in a water vapor cloud.

The onboard system comprises one or more infrared sensors positioned on the aircraft to face downstream along the jet engine exhaust, and configured to discriminate ash emission from the normal infrared emission of jet engine exhaust. The sensor's field of view includes atmosphere that has been heated by passage through a jet engine. The heat of the engine evaporates the precipitate particles, exposing the embedded ash particles to detection by the infrared sensor.

The sensor is configured to measure the thermal infrared emission from the jet engine exhaust, and detect an anomalous rise therein. The detection system then generates a detection signal when the anomalous rise in thermal infrared emission exceeds a user-specified or pre-determined threshold.

Other aspects of the invention are disclosed and claimed below.

BRIEF DESCRIPTION OF THE DRAWINGS

Reference will hereinafter be made to the drawings in which similar elements in different drawings bear the same reference numerals.

DETAILED DESCRIPTION

Figure 1:
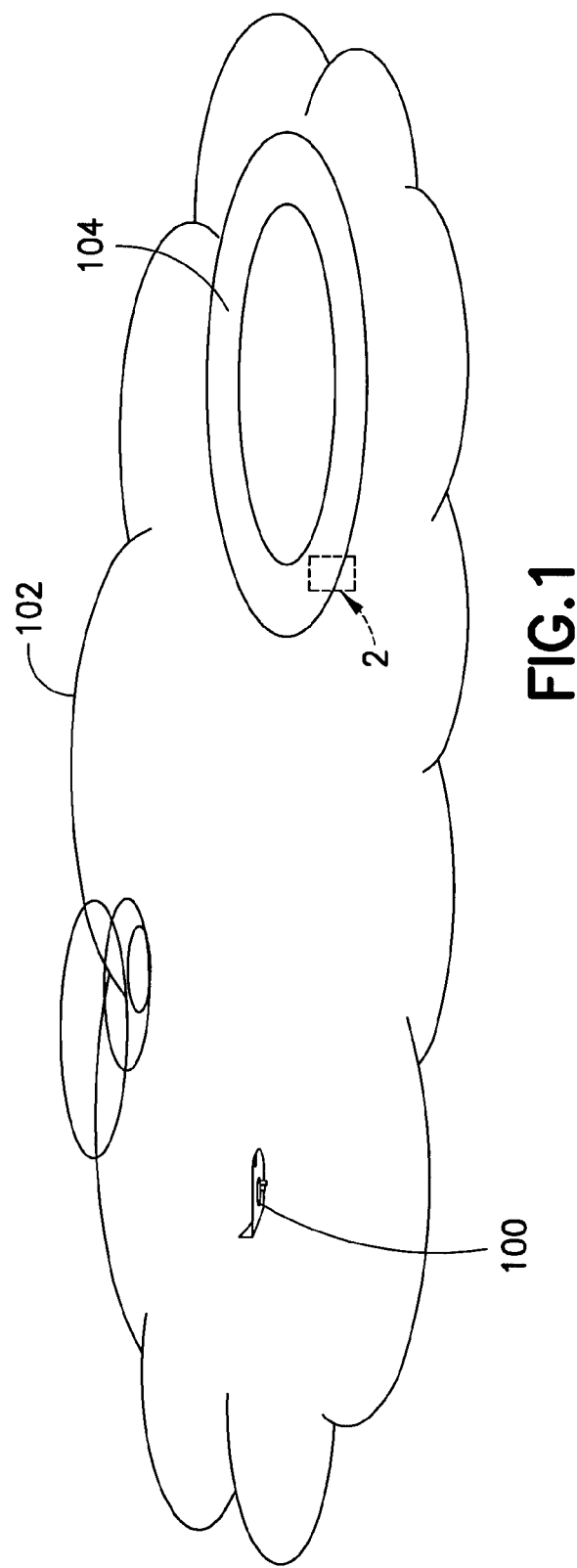
FIG. 1 is a diagram (not to scale) showing an aircraft flying towards a water vapor cloud containing embedded particles of volcanic ash.
Figure 2:
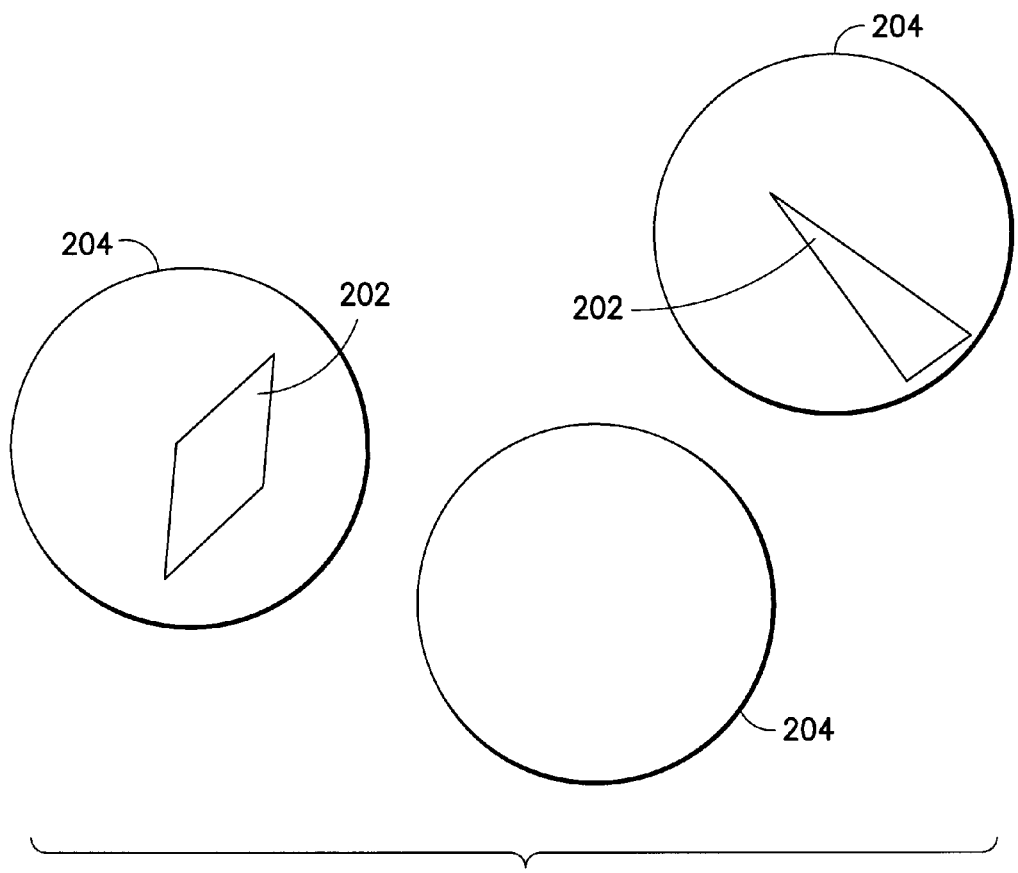
FIG. 2 is a diagram showing a close-up of the inside of a water vapor cloud containing particles of volcanic ash embedded in precipitate particles.

The present disclosure provides systems and methods for early detection of volcanic ash embedded in clouds. In FIG. 1, aircraft 100 is depicted flying towards a water vapor cloud 102 having volcanic ash 104. In FIG. 2, a close-up of the water vapor cloud 102 is shown, in which particles of volcanic ash 202 are embedded in water droplets 204. Although described below as embedded in water droplets 204, volcanic ash particles 202 may also be embedded in crystals of ice.

Figure 3:
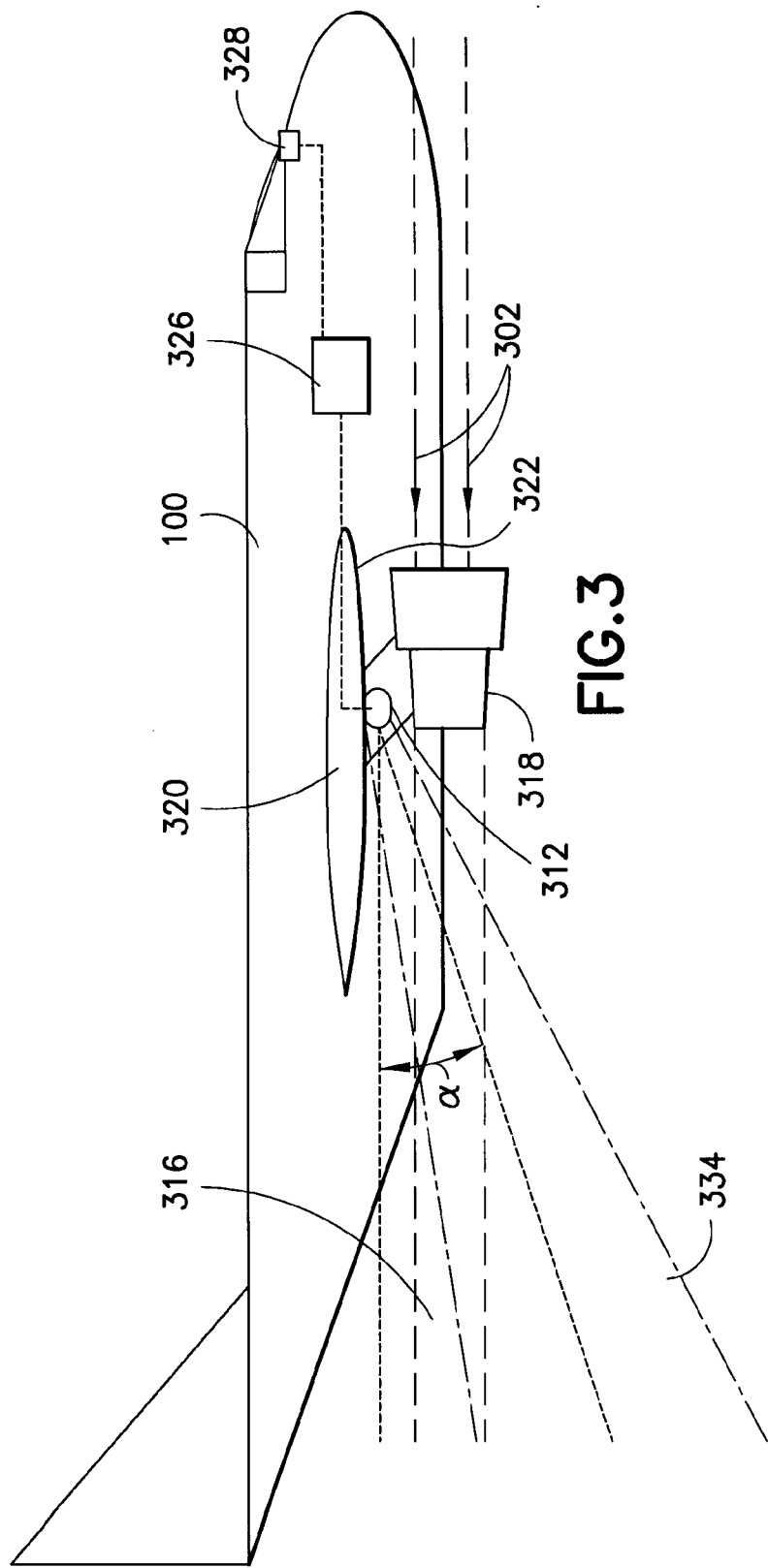
FIG. 3 is a diagram showing a system for detection of volcanic ash particles, installed on an aircraft that has flown through a water vapor cloud containing embedded particles of volcanic ash and which is leaving a trail of jet exhaust containing heated and exposed volcanic ash particles.

Detection of volcanic ash in water vapor clouds using the disclosure provided herein is done after an aircraft 100 has already flown through at least a portion of a water vapor cloud 102 containing volcanic ash particles 202, as shown in FIG. 3.

When an aircraft passes through a water vapor cloud containing volcanic ash, incoming air 302 containing water vapor and volcanic ash particles 202 enters the engine 318. Some of the ash particles pass directly through, and become heated by, the jet engine of the aircraft. This has two effects. First, the water vapor in droplets having embedded ash particles is boiled off due to the high temperature of jet engine combustion, removing the ash particles from within the droplets and exposing the ash particles (or if embedded in ice crystals, the ice is similarly melted and boiled off, exposing the particles of volcanic ash). Second, the ash particles become heated. Thermal characteristics of these heated ash particles allow detection by infrared (also referred to herein as "IR") sensors configured to search for specific electromagnetic radiation emissions in the infrared band of the electromagnetic spectrum. As used herein, the terms "infrared emissions" and "infrared radiation" have the same meaning and refer to electromagnetic radiation in the infrared band of the electromagnetic spectrum. Jet exhaust 316 contains heated ash particles, heated soot particles, and heated gasses. Soot particles are byproducts of hydrocarbon combustion and consist of complex hydrocarbon molecules. Soot particles in the jet exhaust 316 are heated to a similar temperature as the ash particles.

Figure 4:
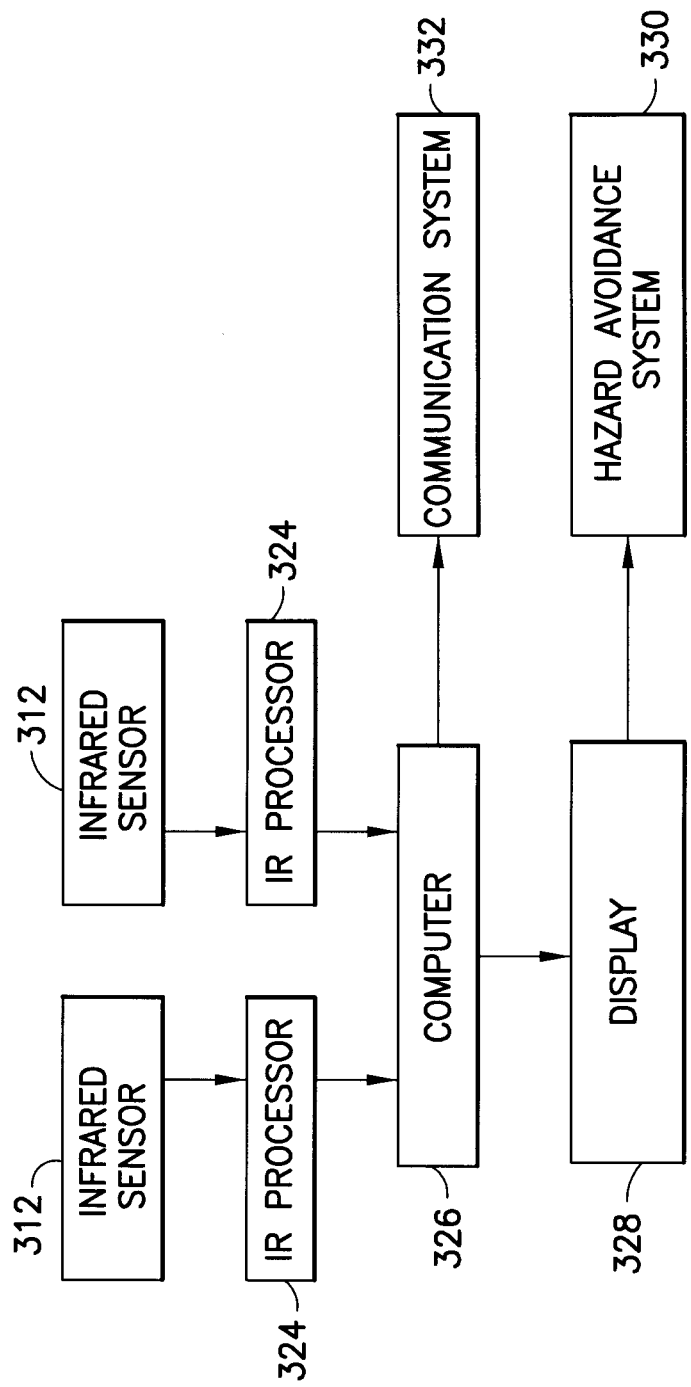
FIG. 4 is a block diagram of a system for detection of volcanic ash particles embedded in a water vapor cloud.

A system having an infrared sensor directed at the exhaust of a jet engine can therefore be used to detect the presence of ash. Such a system is depicted integrated with an airplane in FIG. 3 and as a block diagram in FIG. 4. Multiple infrared sensors are shown in FIG. 4. These represent sensors that may be placed at different locations on an aircraft to view exhaust from different jet engines. If the system 304 detects infrared radiation indicative of volcanic ash particles, then a notification signal is sent to an aircraft central control system 326, also referred to herein as "computer," which can in turn inform the pilot that the aircraft has flown through a water vapor cloud containing volcanic ash. The pilot may then take any necessary corrective measures, which may include throttling back the engines and alteration of the aircraft's course to avoid the volcanic ash. Because the system 304 allows detection of ash prior to engine failure, flight through ash is avoided for a substantial time interval, thereby preventing additional damage by the ash to the aircraft parts.

The system comprises an infrared sensor 312 coupled to a location on an aircraft 100 from which jet engine 318 exhaust 316 may be optically monitored by the sensor 312. The sensor 312 may be a standard infrared sensor capable of withstanding conditions present on the external surface of an aircraft fuselage during flight—namely, high wind, vibration and low temperature, and should be able to discern infrared intensity and wavelengths accurately. In the embodiment depicted in FIG. 3, jet engine 318 extends downward from wing 320, so that an infrared sensor 312 located on the underside 322 of wing 320 can be directed such that it views the exhaust 316 without being blocked by other portions of the aircraft 100. It should be recognized that a large variety of aircraft jet engine configurations exist, and that placement of the sensor on the bottom side of a wing is simply an exemplary configuration which may be utilized in the aircraft jet engine configuration depicted in FIG. 3.

Infrared sensor 312 is coupled to a volcanic ash infrared signature processing component 324 (also referred to herein as an "IR processor"). The IR processor 324 receives raw data from the IR sensor 312 and analyzes the data to determine whether volcanic ash is present in the jet engine exhaust 316. The IR processor 324 may be coupled to an aircraft central control system/computer 326. The IR processor 324 may be any component capable of analyzing the raw data provided by the IR sensor 312 and reasonably discerning the presence of volcanic ash from that raw data. Examples of such a component include a digital processor coupled to digital memory containing instructions for analyzing the raw data from the sensor in order to determine the presence of volcanic ash, or an analog circuit built to make required calculations. The IR processor 324 may be either a standalone, separate physical component or may be a programmed set of instructions entered into a component of the aircraft that would be otherwise present.

The computer 326 can alert a pilot that ash is present through the use of a display 328, and the pilot may take appropriate action. Optionally, the computer 326 may automatically take action upon detection of ash, utilizing a hazard avoidance system 330. For example, if a severe level of ash is detected, the system may automatically throttle back the engines and drop altitude, or may do so after prompting the pilot. Optionally, the computer 326 may relay information about the presence of volcanic ash to other aircraft or to ground based computer through the use of communications system 332.

Preferably, infrared sensor 312 is oriented to maximize the discernability of the IR signature generated from the heated volcanic ash particles. All objects emit blackbody radiation with a spectral peak wavelength inversely proportional to their temperature. This includes atmospheric gasses, aircraft components, solid particulates suspended in air, such as ash and soot, as well as other objects. A "spectral peak," for data consisting of a plot of wavelength versus intensity, is a local maximum in intensity. A "spectral peak wavelength" is the wavelength at which that local maximum occurs. An ideal black body radiation curve for an ideal black body at a given temperature has a single spectral peak having a single spectral peak wavelength. In the temperature ranges present on earth, all objects emit significant blackbody radiation in the infrared band of the electromagnetic radiation spectrum. Therefore, an IR sensor directed at jet exhaust will detect IR radiation emitted from objects other than simply the heated ash particles. However, the IR emitted from ash particles can be distinguished from other normally detected IR radiation in several ways.

Preferably, it should be ensured that the IR sensor 312 is pointed away from any solid aircraft part, especially heated parts of the aircraft 100 near the engine 318 and the engine 318 itself. This is because the solid aircraft 100 parts such as the engine 318 emit a large amount of IR radiation at wavelengths similar to that of the hot ash. If the IR sensor 312 is oriented such that it receives IR radiation from solid aircraft parts, the signal from the solid aircraft parts may "drown out" the signal from the ash, and it will be difficult or impossible to discern an IR signal from the ash.

Therefore, preferably, infrared sensor 312 should be pointed to view only the exhaust 316 from the jet engine 318, such that IR sensor 312 detects only IR emissions from a) the heated exhaust gasses which exit the jet engine; b) any heated soot particles which exit the engine; c) any heated volcanic ash particles which exit the engine; and d) the unheated background atmosphere. Solid aircraft parts are excluded from this view. The IR sensor 312 may have a feature for limiting the scope of view of the sensor IR. For example, a peripheral shield may be used to block electromagnetic radiation from locations outside of a defined scope of vision. This may assist in blocking out emissions from solid aircraft components.

For the aircraft 100 depicted in FIG. 3, the infrared sensor 312 is pointed at an angle α in a direction that corresponds to roughly 10° to 45° downward with respect to the length of the aircraft 100, and facing towards the rear of the aircraft 100. This allows the sensor 312 to avoid viewing solid parts of the aircraft 100, while also allowing the sensor 312 to view exhaust 316 that retains sufficient heat from the jet engine 318. If the sensor 312 is pointed too far downward, there is a risk of picking up emissions from solid aircraft parts, while if the sensor is pointed too far backwards (e.g., less than approximately 10° downward with respect to the front-to-back axis), then it will not view sufficiently heated aircraft exhaust 316. If the exhaust 316 viewed is not sufficiently heated, then the signal-to-noise ratio of the IR signal from ash particles may be too low, in which case any emissions from volcanic ash particles may not be distinguishable over noise. Depending on the position of the IR sensor 312 on the wing, the IR sensor may have to be directed to the left or to the right in order to be facing the jet engine exhaust 316. When positioning the sensor on the wing, it should be kept in mind that the sensor should be positioned to avoid viewing solid aircraft parts.

With the IR sensor 312 pointed away from any solid aircraft parts, the IR signal from the ash may be distinguished from the IR emitted from other emitters of a significant amount of blackbody radiation in the vicinity of the aircraft.

The surrounding atmosphere 334, which is unheated, emits a different radiation pattern than that emitted by components of the heated jet exhaust 316, including heated gasses, volcanic ash and soot. The temperature of jet exhaust 316, including ash particles which exit from jet engines 318 is typically around 900K to 1100K. Because all objects emit black body radiation having a spectral peak wavelength inversely proportional to their temperature, the temperature of the ash particles produces an IR pattern having a spectral peak different from that of the much cooler surrounding atmosphere.

Unheated, surrounding atmospheric gasses 334 have a temperature that varies with altitude of the aircraft 100. For example, at 30,000 feet above sea level, average temperature is approximately −47.83° F. or 228.8K. At 35,000 feet, the temperature is approximately −65.61° F. or 218.9222K. Spectral peak for gas at this temperature is approximately 12.7 microns. This temperature is much lower than the temperature of jet exhaust 316 near the engine 318. Because the intensity of blackbody radiation for any object at a given temperature drops off sharply for wavelengths substantially lower than the spectral peak wavelength of the blackbody radiation pattern for that temperature, the contribution of blackbody radiation of the cool atmospheric gasses 334 to the emission of the heated jet exhaust 316 at the spectral peak wavelength is virtually zero. Emissions from heated jet exhaust 316 may therefore be easily distinguished from surrounding atmosphere by simply examining the intensity of infrared radiation at or near the spectral peak wavelength for the exhaust emissions 316 and ignoring emissions near the spectral peak wavelength for the cooled atmosphere. It should be recognized that IR emissions need not be examined at the precise spectral peak wavelength for the exhaust emissions 316. A range of IR wavelengths or "spectral window" surrounding or near the precise spectral peak wavelength for the heated exhaust may be examined with similar result.

All components of the exhaust from the engines 316 are heated to approximately the same temperature. This includes the exhaust gasses, as well as soot particles and any volcanic ash particles present. Because solid particles are much stronger IR emitters than gasses, IR emissions at the spectral peak wavelength for the heated exhaust 316 will be dominated by emissions from the soot particles and any volcanic ash particles that are present. In order to determine whether there is any volcanic ash in these emissions, intensity of IR emissions at the spectral peak wavelength is constantly monitored to determine whether there is an anomalous rise corresponding to the presence of additional solid particulates—namely, volcanic ash particles. A sufficient rise in IR radiation at or near this spectral peak wavelength will almost always indicate the presence of additional solid particulates in the form of volcanic ash particles. At cruise altitude in the stratosphere, volcanic ash is virtually the only form of solid particulate present in sufficient concentrations to cause such a rise in IR radiation. Neither dust storms nor smoke from fires typically reach as high as cruise altitude. A notable exception is smoke and dust from large nuclear explosions or dust from dust storms within the troposphere. Such smoke and dust may also cause an anomalous rise in IR radiation and be detected as volcanic ash by the system. However, because such particulates should be avoided by aircraft as well, detection by the system is beneficial.

Figure 5:
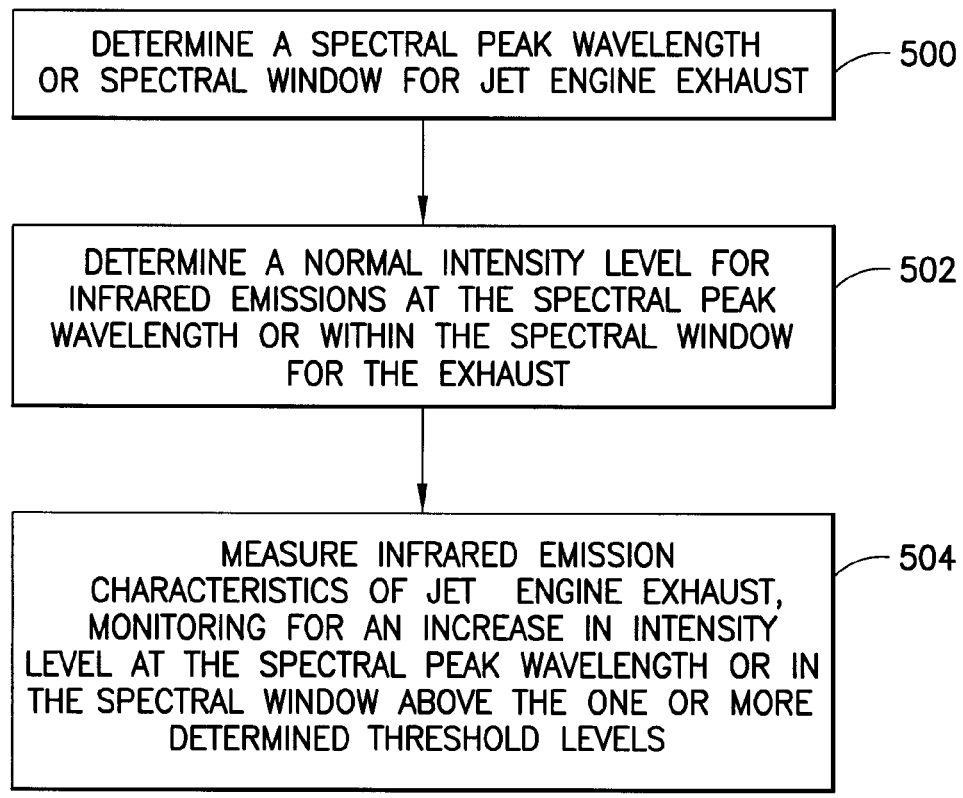
FIG. 5 depicts steps in a method for detection of volcanic ash particles embedded in a water vapor cloud.

A method for determining whether there is an anomalous rise in intensity at the spectral peak wavelength corresponding to heated volcanic ash is presented in FIG. 5.

In step 500, the spectral peak wavelength for jet engine exhaust at present flight conditions is determined. This may be done by determining the temperature of the jet exhaust 316 at the location being examined and applying Wien's displacement law to calculate the spectral peak wavelength ($\lambda_{max}$) for the given temperature. Wien's displacement law allows calculation of the spectral peak wavelength ($\lambda_{max}$) for an ideal black body at a given temperature. It states that $\lambda_{max}=b/T$, where T is the temperature of the ideal black body and b is Wien's displacement constant, equal to $2.8977685\times10^{-3}$ m·K. Using this law, the wavelength spectral peak of the black body radiation for jet exhaust at 1000K can be calculated as $2.8977685\times10^{-3}$ m·K/1000K=$2.8977685\times10^{-6}$ m=approximately 3 microns. It would be desirable to monitor emissions at this wavelength to detect the presence of volcanic ash. However, because water molecules in the atmosphere have a strong absorption peak from about 2.3 to 3.2 microns, it would be difficult to get a good measurement of IR emissions from volcanic ash within that range. Therefore, a range of wavelengths outside of this water molecule absorption peak range is chosen to obtain a strong signal from volcanic ash. A range of between 3.2 and 3.4 microns is an appropriate range to monitor for this purpose.

In step 502, the "normal" or "steady state" intensity level for infrared emissions at or near the spectral peak wavelength for the exhaust is determined. This "steady state" intensity level is caused primarily by soot exiting from the engines. It is therefore equivalent to the intensity of infrared radiation emitted by that soot. The amount of soot that exits the engine, and therefore the "steady state" intensity level, may vary depending on the current flight conditions. However, an abrupt rise in intensity, as opposed to a "steady" radiation intensity level, at constant or slowly changing flight conditions may indicate the presence of additional IR emitters beyond the expected amount of soot. The speed of such a rise which may indicate an undesirable level of volcanic ash in the jet exhaust may be a user selectable parameter based on how sensitive a user, such as a pilot or technician, wishes the system to be. Some such users would prefer more warnings, while others will tolerate fewer false alarms and will only wish to get warnings about very serious encounters. Exemplary values for anomalous time periods for IR intensity increases are one minute for a relatively small rise (for example, a 20% rise) or ten minutes for a large rise (for example, a 100% rise). The presence of additional emitters in the form of volcanic ash would cause the intensity of the radiation emitted at the spectral peak wavelength to increase by a certain factor (an "anomaly" factor) depending on the amount of ash in the exhaust 316.

In step 504, the intensity at this spectral peak wavelength is monitored for an increase above an intensity level threshold corresponding to an undesirable amount of volcanic ash. The intensity threshold may be determined in a number of ways.

In a first way, the threshold is dependent on the ratio of an elevated concentration of particulates (such as ash and soot), including an undesirable concentration of volcanic ash, to a normal concentration of solid particulates including only the normal level of soot. Because intensity of blackbody radiation emitted by solid particulates suspended in air increases in proportion to the concentration of the solid particulates, the intensity threshold can be calculated as a percent increase over the steady state intensity level of IR at the spectral peak wavelength as follows. In the calculations below, $C_a$ is equivalent to an undesirable concentration of ash in the jet exhaust, $C_s$ is equivalent to a normal concentration of soot in the jet engine exhaust, $C_p$ is equivalent to $C_a+C_s$ which is equivalent to the total particulate concentration including an undesirable amount of ash, $I_n$ is equivalent to the "normal" or "steady state" intensity level at the spectral peak wavelength, and $I_t$ is equivalent to the intensity level threshold at the spectral peak wavelength which indicates an undesirable amount of volcanic ash in the jet engine exhaust. The following calculations begin with the assumption that the intensity level of the radiation at the spectral peak wavelength increases in direct proportion to any increase in concentration of solid particulates. Therefore, the ratio of an increased concentration of particulates to the normal concentration of particulates is equivalent to the ratio of an increased intensity level to a normal intensity level.

$$(C_a+C_s)/C_s=I_t/I_n$$

$$I_t=I_n(C_a+C_s)/C_s$$

$$I_t=C_p/C_s\times I_n$$

In other words, a threshold intensity level can be defined as the ratio of a total particulate concentration with undesirable amount of ash to the "normal" particulate concentration times the normal intensity level of infrared at the spectral peak wavelength. If this threshold intensity level is detected, then there is an undesirable amount of volcanic ash in the engine exhaust.

If desired, several threshold intensity levels, for example, $I_{t1}$, $I_{t2}$, may exist which correspond to different concentrations of volcanic ash, for example $C_{a1}$, $C_{a2}$, etc. Different warnings may be given to the pilot at each concentration. For example, a first concentration may indicate the presence of a level of ash that may require enhanced maintenance procedures after a flight while a second, higher concentration may indicate the need for repair or replacement of parts after a flight.

Another method of determining a threshold intensity level is by determining the highest concentration of soot reasonably possible for given flight conditions, determining a corresponding intensity level (a "maximum intensity level") of infrared emissions at the corresponding spectral peak wavelength, and determining an increment above which there is reasonable confidence that an undesirable concentration of volcanic ash must be present. The increment may be represented as a percentage. For example, an increment of 15% may be chosen such that the threshold intensity level is equal to the maximum intensity level times 115%. An increment may also be chosen such that it is below the threshold intensity level calculated using the ratio of undesired particulate concentrations to normal particulate concentrations, as explained above. Thus if the ratio of undesired particulates to normal particulates is 2 to 1 (therefore, a 100% increase), the increment may be chosen as 50%, which is less than 100%.

Figure 6:
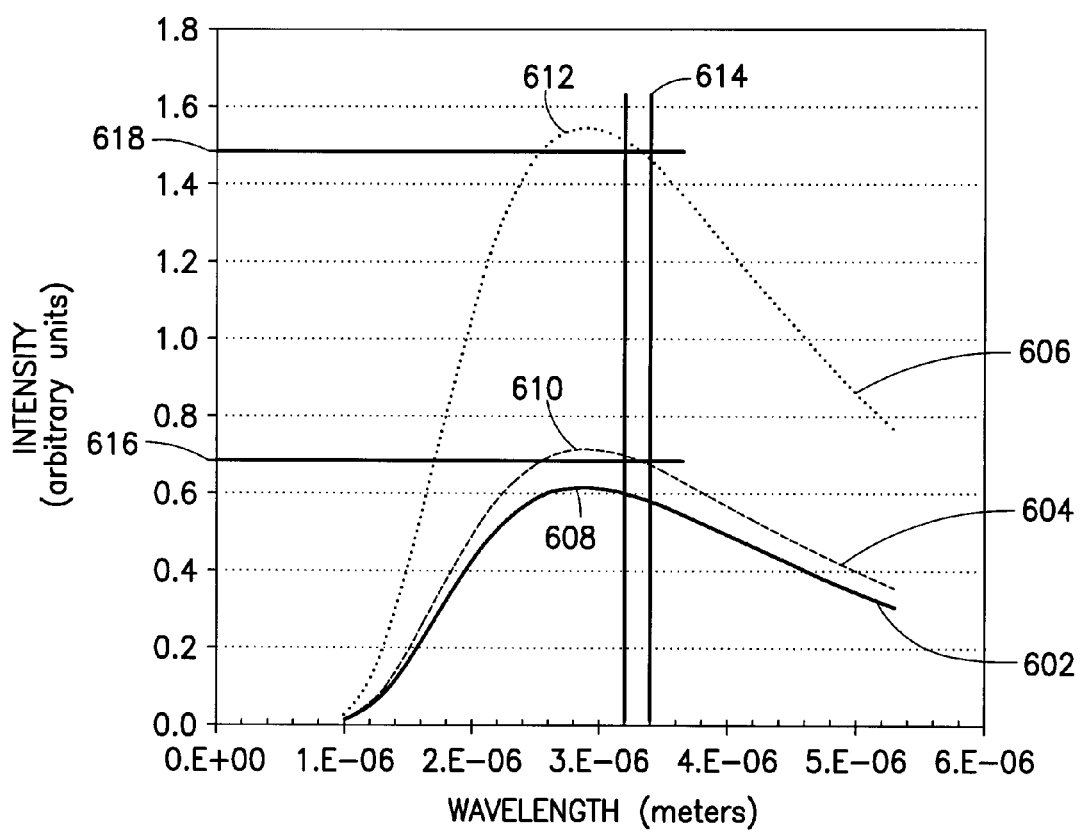
FIG. 6 is a graph showing estimated infrared emissions detected by the infrared sensors located and oriented as described herein.

FIG. 6 depicts an estimation of blackbody radiation as detected by infrared sensor for a number of different ash concentrations: no ash 602, some ash 604, and a dangerous level of ash 606. Spectral peaks 608, 610, 612 for each of the curves are shown. Each level of ash has a broad spectral curve. A window 614 is shown, which corresponds to a range of approximately 3.2 to 3.4 microns in wavelength. To determine an intensity level, the system may average the intensity levels measured within this window 614. Example average intensity levels within the window 614 are depicted as horizontal lines in FIG. 6. The average intensity level for the "some ash" curve 604 is line 616 and for the "dangerous ash" curve 606, the average intensity level is line 618. The example values shown in FIG. 6 for the three curves shown are 0.58 arbitrary units for no ash, 0.68 arbitrary units for some ash and 1.48 arbitrary units for a dangerous level of ash.

Example calculations will now be provided to illustrate the concepts discussed above. It is generally accepted that soot is emitted from jet engines at a rate of 0.04 g per kilogram of fuel burned. This translates to a concentration of soot equal to approximately $3.3 \times 10^{-4}$ g/m$^3$ at the nozzle. In other words, a standard concentration of soot in the jet engine exhaust for these numbers is approximately $3.3 \times 10^{-4}$ g/m$^3$. A normal intensity level of IR radiation in the spectral window for this soot is measured. This normal intensity level can be labeled a 100% intensity level and corresponds to the "no ash" curve 602 in FIG. 6.

Undesirable concentrations of ash are determined. In these example calculations, numbers from European flight guidelines for dangerous concentrations of volcanic ash are provided. In Europe, the threshold of ash concentration at which aircraft must undergo enhanced maintenance procedures is $2 \times 10^{-4}$ g/m$^3$ and the threshold of ash concentration at which aircraft should not fly is $2 \times 10^{-3}$ g/m$^3$. Allowing for thermal expansion of air heated in the engine, these values translate to $5 \times 10^{-5}$ g/m$^3$ in the jet engine exhaust for enhanced maintenance procedures and $5 \times 10^{-4}$ g/m$^3$ in the jet engine exhaust for the no-fly threshold.

The total undesirable concentration of particulates (soot plus ash) for the enhanced maintenance procedures is equivalent to $3.3 \times 10^{-4}$ g/m$^3$ + $5 \times 10^{-5}$ g/m$^3$ = $3.8 \times 10^{-4}$ g/m$^3$. The ratio of total undesirable particulates to normal particulates is 3.8 to 3.3 which is equivalent to 115%. Thus a first threshold may be set at 115% of normal IR emissions (shown as the first threshold line 616 in FIG. 6) or may be set to a value between 100% and 115%. Observation of IR emissions in the spectral window which meet this threshold would indicate a concentration of ash requiring enhanced maintenance procedures, which typically include more frequent inspection of turbine blades and of hot surfaces inside jet engines.

The total undesirable concentration of particulates (soot plus ash) for the no-fly threshold is equivalent to $3.3 \times 10^{-4}$ g/m$^3$ + $5 \times 10^{-4}$ g/m$^3$ = $8.3 \times 10^{-4}$ g/m$^3$. The ratio of total undesirable particulates to normal particulates is 8.3 to 3.3 which is equivalent to 250%. Thus a second threshold may be set at 250% of normal IR emissions (depicted as the second threshold line 618 in FIG. 6) or may be set to a value between 100% and 250%. Observation of IR emissions in the spectral window 614 which meet this threshold would indicate a concentration of ash indicating that an aircraft should not fly in that area.

FIGS. 7A-7D depict several other aircraft engine configurations and corresponding exemplary sensor locations. In each of these figures, the sensor orientation is chosen in line with the principles described above—namely, the sensor should be oriented such that the sensor views jet engine exhaust in close proximity to the engine exit, which therefore retains significant heat but such that the sensor does not detect IR radiation from solid aircraft parts.

Figure 7A:
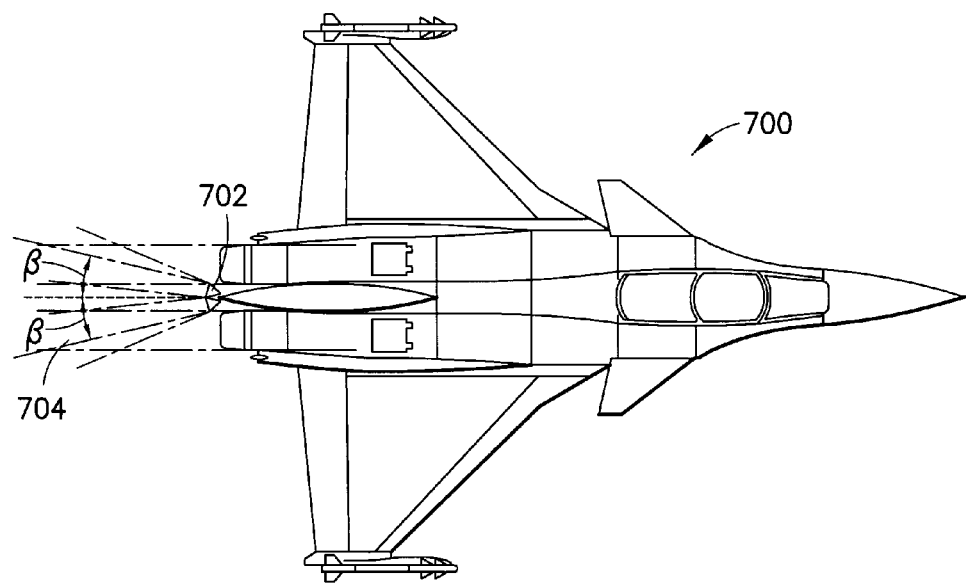
FIGS. 7A-7D depict additional jet engine configurations and exemplary placement and orientation of sensors for detecting ash appropriate for those jet engine configurations.
Figure 7B:
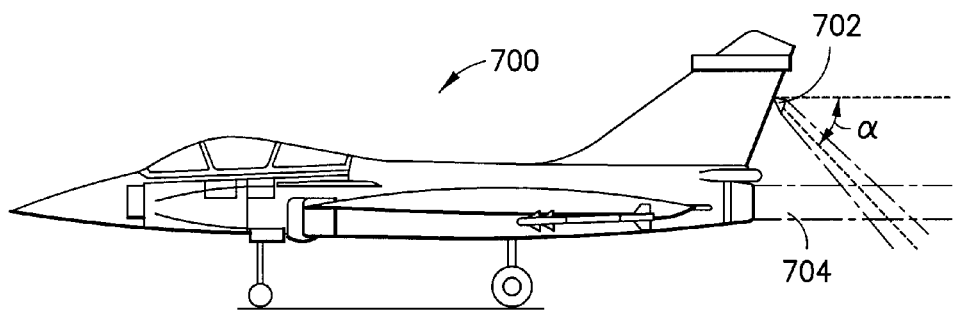

FIGS. 7A-7B depict a twin-engine aircraft 700 in which each engine is enclosed within the fuselage. The exhaust 704 exits the engines at the rear of the aircraft. Infrared sensors 702 may be placed at any location on the aircraft at which exhaust is viewable while the solid aircraft body is excluded from view. One location for sensors in this configuration is at the tail of the aircraft. At this location, the sensors can be pointed downwards by approximately 10°-45° with respect to the length of the aircraft, and can be pointed to an angle of slightly less than 10° to the left or right. In such an orientation, exhaust from the engines is viewable and solid aircraft components are excluded from view.

Figure 7C:
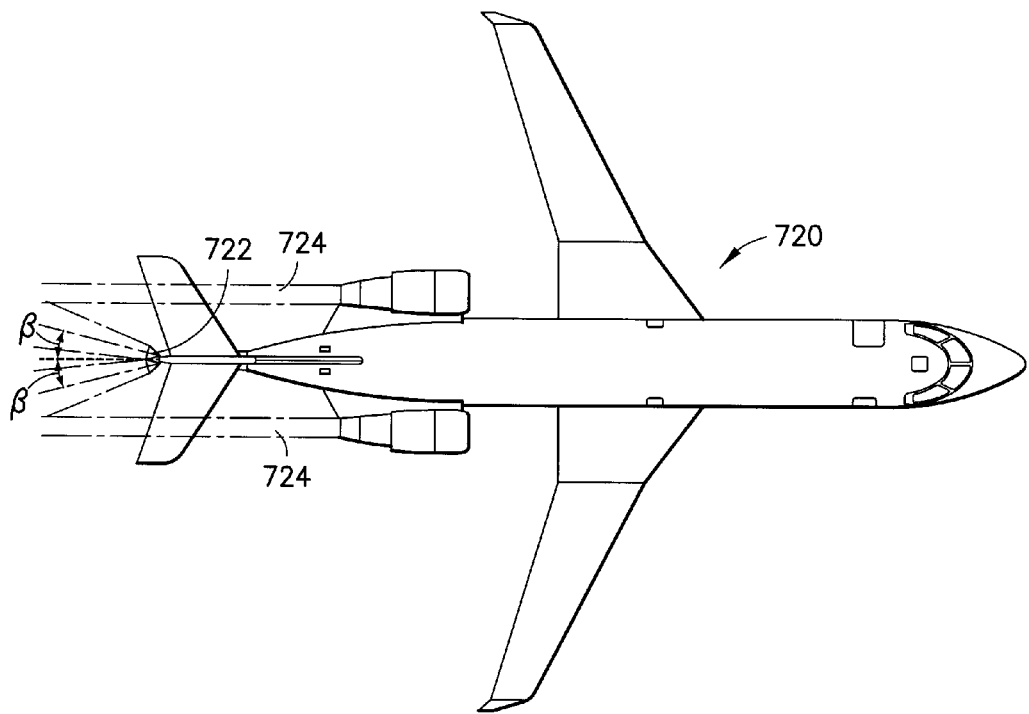
Figure 7D:
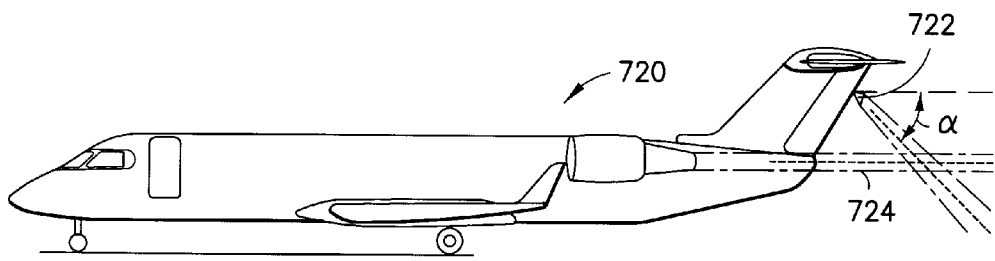

FIGS. 7C-7D depicts a twinjet configuration aircraft 720 in which two engines are attached to the fuselage to the rear of the wings and extend to the side of the aircraft 720. In such a configuration, an appropriate location for infrared sensors 722 would also be on the tail of the aircraft. At this location, sensors may be pointed downwards by approximately 10°-45° with respect to the length of the aircraft, and can be pointed straight downward by 90° with respect to the width of the aircraft.

Although the embodiments disclosed so far involve measurements made on a single airplane, further embodiments use measurements made aboard multiple aircraft, the measurement data being relayed to a ground-based central processing site. The central processing site comprises a computer that combines the measurements from all aircraft, together with locations and times at which the measurements were made, meteorological data, and information about plausible volcanic sites, to better estimate the location and other characteristics of the ash plumes.

In particular, the central processing site may comprise a data fusion system that receives infrared emission measurements from multiple aircraft and combines them to form an estimate of a plume's characteristics and, optionally, construct a three-dimensional model of the plume. In this case, each of a plurality aircraft transmits a respective set of infrared emission measurements (and associated metadata, such as time and location of the aircraft) to a data fusion center via a network. More specifically, each aircraft comprises a transmitter and an antenna for wireless communication with the network. All measurements are incorporated into the data fusion system and are used to detect the presence of a volcanic plume and estimate the plume's characteristics. Optionally, the data fusion system also constructs a three-dimensional model of the plume. When the measured gas concentrations from multiple aircraft indicate the presence of a volcanic plume, the data fusion system generates a warning to a human controller, e.g., a visual warning which is displayed by a controller warning display. The particular fusion algorithm or approach may vary.

There are several known hardware/software systems that combine observations of phenomena from multiple mobile sensors to create a better estimate than any single sensor could make on its own.

For example, meteorological measurements from diverse balloons and aircraft are transmitted via radio links and ground networks to a workstation. The workstation runs a software program called 4DVAR, which uses a variational cost-minimization approach to fuse data from multiple sensors at various times and places. (A technical summary of the 4DVAR method can be found in the publication "Data assimilation concepts and methods", F. Boutier and P. Courtier, March 1999, Meteorological Training Course Lecture Series, copyright ECMWF 2002, available at http://www.ecmwf.int/newsevents/training/rcourse_notes/DATA_ASSIMILATION/ASSIM_CONCEPTS/Assim_concepts11.html, the contents of which are incorporated by reference herein in its entirety.) Its output is an atmosphere model that is more accurate than an analysis could produce from a lone sensor.

Another example is military radar. Military radar observations from multiple ground and airborne radars are transmitted via various networks to a workstation. The workstation runs a Bayesian software model that combines evidence from various radar measurements to accurately track a hostile aircraft.

These methods are well known to persons skilled in the art of data fusion. Compared to the general meteorology case, in which many different kinds of data are combined, the process of transmitting and combining infrared emission measurements (a single kind of data) from different aircraft should not require undue experimentation by persons skilled in the art.

Installing and monitoring IR sensors in accordance with this disclosure on multiple aircraft that communicate with a network improves the chance to detect and characterize a volcanic plume before it damages any aircraft. A warning signal from the first aircraft to detect the plume can be relayed to all aircraft in the area, even those without ash plume detection systems.

In summary, the embodiments disclosed herein provide distinct advantages as compared to prior solutions for detecting the presence of volcanic ash, because no methods exist for detection of ash particles embedded in water vapor clouds.

Furthermore, the embodiments disclosed herein provide direct warning to an airplane's pilot rather than relying on the process to issue a notice to airmen.

While several exemplary embodiments have been disclosed, it will be understood by those skilled in the art that various changes may be made and equivalents may be substituted for elements thereof without departing from the scope of this disclosure. In addition, many modifications may be made to adapt a particular situation to the teachings of this disclosure without departing from the essential scope thereof. Therefore it is intended that the disclosure not be limited to the particular embodiments disclosed for carrying out the teachings of this disclosure.

The invention claimed is:

1. A method for detecting volcanic ash embedded in a water vapor cloud, comprising the following steps:
    measuring an intensity of infrared radiation emissions of a jet engine exhaust at or near a spectral peak wavelength for the jet engine exhaust; and
    generating a detection signal indicating the presence of volcanic ash in the jet engine exhaust when the intensity of infrared radiation emissions at or near the spectral peak wavelength exceeds a threshold.

2. The method of claim 1, wherein the threshold is determined by:
    determining a normal intensity of infrared radiation emissions at the spectral peak wavelength during flight in which substantially no volcanic ash is present in the jet engine exhaust;
    identifying a normal concentration of soot present in the jet engine exhaust;
    identifying a first unwanted concentration of volcanic ash;
    calculating a total unwanted particulate concentration by adding said normal concentration to said first unwanted concentration;
    calculating a first concentration ratio by dividing said total unwanted particulate concentration by said normal concentration; and
    multiplying said normal intensity by said first concentration ratio to determine said threshold.

3. The method of claim 1, wherein the threshold is determined by:
    determining a normal intensity of infrared emissions at the spectral peak wavelength during flight in which substantially no volcanic ash is present in the jet exhaust;
    identifying a normal concentration of soot present in the jet engine exhaust;
    identifying a first unwanted concentration of volcanic ash;
    calculating a total unwanted particulate concentration by adding said normal concentration to said first unwanted concentration;
    calculating a first concentration ratio by dividing said total unwanted particulate concentration by said normal concentration; and
    multiplying said normal intensity by said first concentration ratio to determine a maximum intensity threshold; and
    setting said threshold to a value in between said normal intensity and said maximum intensity threshold.

4. The method of claim 1, further comprising:
notifying a pilot when the detection signal is generated.

5. The method of claim 1, further comprising:
automatically throttling back the engine when said detection signal is generated.

6. The method of claim 1, further comprising:
notifying a central processing site of the presence of volcanic ash when said detection signal is generated.

7. The method of claim 1, wherein:
measuring the intensity of infrared radiations emissions comprises continually monitoring the intensity of light emitted at or near a determined spectral peak wavelength.

8. The method of claim 1, further comprising:
providing an infrared sensor;
coupling said sensor to an aircraft at a location from which jet engine emissions are viewable; and
orienting said infrared sensor such that substantially no solid parts of the aircraft are viewable by the sensor.

9. A system for detecting volcanic ash embedded in a water vapor cloud, comprising:
    an infrared sensor located and oriented to view jet engine exhaust; and
    an infrared (IR) processor receiving raw data from said infrared sensor and determining when an amount of volcanic ash above a threshold level is present.

10. The system of claim 9, wherein said infrared sensor is mounted on an aircraft.

11. The system of claim 10, wherein said aircraft has a jet engine extending downwards from a wing, said infrared sensor is mounted on a bottom side of said wing, and said infrared sensor is pointed rearwards by an angle of between approximately 10° and approximately 45° relative to the length of the aircraft.

12. The system of claim 9, wherein said IR processor is programmed to generate a detection signal when an intensity of infrared emissions at or near a spectral peak wavelength exceeds a threshold.

13. The system of claim 12, wherein said IR processor is programmed to determine said threshold by:
    determining a maximum possible intensity of infrared emissions at the spectral peak wavelength during flight in which substantially no volcanic ash is present in the jet exhaust; and
    multiplying said maximum possible intensity by an increment to determine said threshold.

14. The system of claim 12, wherein said IR processor is programmed to determine said threshold by:
    determining a normal intensity of infrared emissions at the spectral peak wavelength during flight in which substantially no volcanic ash is present in the jet exhaust;
    identifying a normal concentration of soot present in the jet engine exhaust;
    identifying a first unwanted concentration of volcanic ash;

calculating a total unwanted particulate concentration by adding said normal concentration to said first unwanted concentration;

calculating a first concentration ratio by dividing said total unwanted particulate concentration by said normal concentration; and multiplying said normal intensity by said first concentration ratio to determine said threshold.

15. The system of claim 12, wherein said IR processor is programmed to determine said threshold by:

determining a normal intensity of infrared emissions at the spectral peak wavelength during flight in which substantially no volcanic ash is present in the jet exhaust;

identifying a normal concentration of soot present in the jet engine exhaust;

identifying a first unwanted concentration of volcanic ash;

calculating a total unwanted particulate concentration by adding said normal concentration to said first unwanted concentration;

calculating a first concentration ratio by dividing said total unwanted particulate concentration by said normal concentration; and multiplying said normal intensity by said first concentration ratio to determine a maximum intensity threshold; and setting said threshold to a value in between said normal intensity and said maximum intensity threshold.

16. The system of claim 12, further comprising:

a field of view limiting shield coupled to said infrared sensor.

17. The system of claim 9, wherein:

said IR processor is coupled to an aircraft control system.

18. The system of claim 17, wherein:

said aircraft control system is wirelessly linked to a central processing site; and said aircraft control system sends a signal to said central processing site when volcanic ash is detected in water vapor clouds.

19. A method for detecting volcanic ash embedded in a water vapor cloud, comprising the following steps:

determining a maximum possible intensity of infrared radiation emissions from a jet engine exhaust at a spectral peak wavelength during flight in which substantially no volcanic ash is present in the jet engine exhaust and multiplying said maximum possible intensity by an increment to determine a threshold intensity;

measuring an intensity of infrared radiation emissions of a jet engine exhaust at or near the spectral peak wavelength; and generating a detection signal indicating the presence of volcanic ash in the jet engine exhaust when the intensity of infrared radiation emissions at or near the spectral peak wavelength exceeds the threshold.

20. The method of claim 19, further comprising:

automatically throttling back the jet engine when said detection signal is generated.

21. The method of claim 19, further comprising:

notifying a central processing site of the presence of volcanic ash when said detection signal is generated.

22. The method of claim 19, further comprising:

coupling an infrared sensor to an aircraft in a position that permits orienting the sensor to view the infrared radiation emissions of the jet engine exhaust and substantially no solid parts of the aircraft.

\* \* \* \* \*